United States Patent [19]

Amjad

[11] Patent Number: 4,915,937

[45] Date of Patent: * Apr. 10, 1990

[54] DENTAL ANTIHYDROLYSIS AGENT

[75] Inventor: Zahid Amjad, Avon Lake, Ohio

[73] Assignee: The BF Goodrich Company, Akron, Ohio

[*] Notice: The portion of the term of this patent subsequent to Jun. 27, 2006 has been disclaimed.

[21] Appl. No.: 226,587

[22] Filed: Aug. 1, 1988

[51] Int. Cl.$^4$ .......................... A61K 7/16; A61K 7/18
[52] U.S. Cl. ........................................ 424/52; 424/57
[58] Field of Search .................................... 424/52, 57

[56] References Cited

U.S. PATENT DOCUMENTS

| | | | |
|---|---|---|---|
| 4,515,772 | 5/1985 | Parran et al. | 424/52 |
| 4,627,977 | 12/1985 | Gaffar et al. | 424/52 |
| 4,684,518 | 8/1987 | Parran et al. | 424/52 |
| 4,772,461 | 9/1988 | Parran et al. | 424/52 |

*Primary Examiner*—Shep K. Rose
*Attorney, Agent, or Firm*—George A. Kap; Nestor W. Shust

[57] ABSTRACT

Oral compositions and a method for inhibiting tartar on teeth, said compositions comprise a fluoride source, a dental abrasive, and an antihydrolysis agent selected from homopolymers of substituted acrylamides, homopolymers of unsaturated sulfonic acids and salts thereof, and homopolymers and copolymers of cationic monomers. The antihydrolysis agents have molecular weight of 100 to 100,000 and inhibit hydrolysis of polyphosphates to orthophosphates. Whereas polyphosphates generally are effective in inhibiting formation of tartar on teeth, orthophosphates are relatively ineffective.

19 Claims, No Drawings

DENTAL ANTIHYDROLYSIS AGENT

This invention relates to dental compositions containing an antihydrolysis agent for reducing enzymatic hydrolysis of polyphosphates or pyrophosphates and to method for applying such compositions to an oral cavity, particularly teeth.

Tartar or dental calculus is calcified plaque and plaque is the culprit of gum disease. Tartar is a deposit which forms on the surfaces of the teeth at the gingival margin. Mature calculus consists of an inorganic portion which is largely calcium phosphate arranged in a hydroxyapatite crystal lattice structure similar to bone, enamel and dentine. An organic portion is also present and consists of salivary sediment, food debris, and various types of microorganisms.

It is generally agreed that calcium and orthophosphate form the crystalline material known as hydroxyapatite which is dental calculus, i.e., a mineralized, hard formation which forms on teeth. The precursor to crystalline hydroxyapatite is amorphous calcium phosphate which differs from hydroxyapatite in atomic structure, crystal morphology, and stoichiometry. The x-ray diffraction pattern of amorphous calcium phosphate shows broad peaks typical of amorphous materials which lack the long range atomic order characteristic of all crystalline materials, including hydroxyapatite.

It is generally well known that linear molecularly dehydrated polyphosphates, such as hexametaphosphate, tripolyphosphate, pyrophosphate, and the like, are effective calcium and magnesium ion suppressors, inhibitors, sequestrants and/or chelating agents. Such materials are also known to be effective inhibitors of hydroxyapatite formation in vitro. It is also known that such polyphosphates, when introduced into the oral cavity and/or saliva, are significantly hydrolyzed by salivary enzymes to orthophosphates which are ineffective as inhibitors of hydroxyapatite formation.

Studies have shown that there is a good correlation between the ability of a compound to prevent hydroxyapatite crystalline growth in vitro and its ability to prevent calcification in vivo, provided that such compound is stable in and inert to saliva and its components.

REFERENCE TO RELATED APPLICATIONS

Application Ser. No. 135,803 is entitled "Dental Calculus Inhibiting Compositions", was filed Dec. 21, 1987, claims oral compositions and method for inhibiting dental calculus by applying to teeth the composition comprising a fluoride source, a dental abrasive, and an anticalculus agent. The anticalculus agent is selected from homopolymers of monounsaturated carboxylic acids and copolymers thereof containing at least 30% by weight of at least one of said acids. The comonomers are selected from about a dozen monomer classes.

Application Ser. No. 191,667 is entitled "Tartar Inhibition On Teeth", was filed May 9, 1988, claims oral compositions and method for inhibiting tartar by applying to teeth the composition comprising a fluoride source, a dental abrasive, and an anticalculus agent. The anticalculus agent is selected from a mixture of anticalculus agents disclosed in application Ser. No. 135,803.

Application Ser. No. 191,668 is entitled "Tartar Inhibiting Oral Compositions And Method", was filed May 9, 1988, claims oral compositions and method for inhibiting tartar by applying to teeth the composition comprising a fluoride source, a dental abrasive, and an anticalculus agent. The anticalculus agent is a mixture of at least one phosphorus-containing compound and at least one anticalculus agent disclosed in application Ser. No. 135,803.

SUMMARY OF THE INVENTION

Oral compositions claimed herein are characterized by the presence of a fluoride source, dental abrasive, a polyphosphate, and an antihydrolysis agent for inhibiting enzymatic hydrolysis of said polyphosphate in the presence of saliva. This invention is also directed to a method for applying oral compositions disclosed herein to teeth in order to reduce dental calculus by inhibiting hydrolysis of said polyphosphate.

DETAILED DESCRIPTION OF THE INVENTION

The oral compositions of interest herein are characterized by the presence of an effective amount of a fluoride source, an effective amount of a dental abrasive or a polishing agent, an effective amount of a vehicle, an effective amount of at least one polyphosphate, and 0.01 to 10% by weight of an antihydrolysis agent which inhibits hydrolysis of said polyphosphate so that said polyphosphate is not hydrolyzed to an orthophosphate.

The antihydrolysis agent of this invention is selected from homopolymers of substituted acrylamides, homopolymers of unsaturated sulfonic acids, and homopolymers and copolymers of cationic monomers disclosed in U.S. Pat. No. 4,484,631. In the case of homopolymers identified above, a small amount of at least one other comonomer can be included as long as the performance of the homopolymer is not adversely affected. By small amount, it is meant up to about 10% by weight, preferably up to about 5%.

Homopolymers of the monomers noted above and copolymers of carboxylic monomers, which are suitable herein as antihydrolysis agents, have weight average molecular weight in the range of about 100 to 100,000, preferably in the range of about 500 to 50,000 and more preferably in the range of about 2,000 to 20,000. Molecular weight given here is measured by gel permeation chromatography.

Amount of the antihydrolysis agent is 0.01 to 10% by weight, preferably 0.1 to 5% by weight of the entire composition.

Suitable substituted acrylamides are defined as follows:

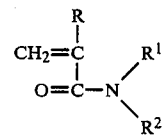

where R is hydrogen or methyl and $R^1$ and $R^2$ are individually selected from hydrogen, alkyl and substituted alkyl groups each containing a total of 1 to 12, preferably 1 to 8 carbons, provided that $R^1$ and $R^2$ are not both hydrogens. Substituents on the alkyl groups include alkyl, aryl, hydroxyl, hydroxyalkyl, carboxylic acid, and keto groups. Specific examples of substituted acrylamides include t-butyl acrylamide, isopropyl acrylamide, isobutyl acrylamide, methyl acrylamide, t-butyl methacrylamide, 2-(2,4,4-trimethyl pentyl) acrylamide, 2-(2-methyl-4-oxopentyl) acrylamide, hydroxymethyl acrylamide, hydroxypropyl acrylamide, diacetone acrylamide, and 3-acrylamido-3-methyl butanoic acid.

Any unsaturated sulfonic acid or its salt can be used in producing the homopolymer which is useful as an antihydrolysis agent herein.

Examples include 2-acrylamido-2-methylpropane sulfonic acid, 2-methacrylamido-2-methylpropane sulfonic acid, vinyl sulfonic acid, sulfo alkyl acrylate or methacrylate, allyl sulfonic acid, styrene sulfonic acid, allyloxyhydroxyalkane sulfonic acids, sulfoalkyl acrylates, methallyl sulfonic acid, 3-methacrylamdo-2-hydroxy propyl sulfonic acid, sulfonic acid acrylate, their salts and mixtures thereof. The preferred sulfonic acids are selected from acrylamidoalkane sulfonic acids, styrene sulfonic acids, allyloxyhydroxyalkane sulfonic acids, and sulfoloweralkyl acrylates.

Acrylamidoalkane sulfonic acids and salts thereof have the following general formula:

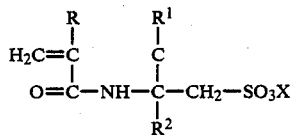

where R is hydrogen or methyl; X is selected from hydrogen, ammonium, alkali metals or alkaline earth metals, particularly hydrogen, ammonium, or an alkali metal; and $R^1$ and $R^2$ are individually selected from hydrogen and alkyl groups of 1 to 4 carbon atoms. In a preferred embodiment, R is hydrogen and $R^1$ and $R^2$ are each an alkyl group of 1 of 3 carbon atoms. The letter X in the above structural formula represents hydrogen or any metal cation which does not adversely affect the water solubility of the polymer, such as sodium, potassium and ammonium cations. In addition, X may also represent calcium, magnesium, and lithium, since they do not present any adverse effects on the solubility of the polymer. The acrylamidoalkane sulfonic acid monomer which has been found to be particularly suitable in accordance with the present invention is 2-acrylamido-2-methylpropane sulfonic acid which has the following structural formula:

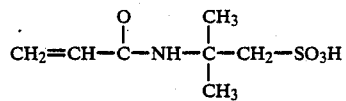

Styrene sulfonic acids and salts thereof suitable herein are defined as follows:

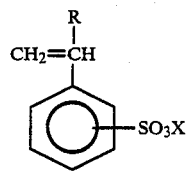

where R is hydrogen or a lower alkyl group of 1 to 6 carbon atoms, but preferably hydrogen, and X is hydrogen, alkali metal or alkaline earth metal or ammonium but particularly hydrogen, ammonium or alkali metal. A particularly suitable sulfonic acid is styrene sulfonic acid where R is hydrogen and the —SO$_3$ group is at the 3 or 4 position on the phenyl ring. The salts of styrene sulfonic acids are water-soluble. The sodium salt of styrene sulfonic acid is available commercially.

Vinyl sulfonic acid and salts thereof are defined as follows:

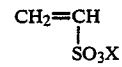

where X is selected from hydrogen, alkali metals, alkaline earth metals, and ammonium radicals.

The allyloxyhydroxyalkane sulfonic acids and salts thereof are defined as follows:

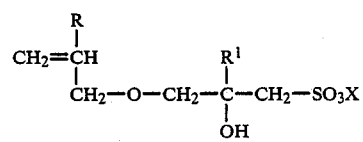

where R and $R^1$ are each hydrogen or methyl, and X is selected from hydrogen, alkali metal, alkaline earth metal and ammonium groups. Preferred monomer in this group is sodium salt of 3-allyloxy-2-hydroxypropanesulfonic acid.

Sulfoalkyl acrylates have the following structure:

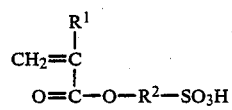

where $R^1$ is selected from hydrogen, methyl and the group

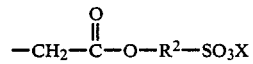

where $R^2$ is selected from alkylene groups of 1 to 12 carbons, preferably 2 to 4 carbons; and where X is selected from hydrogen, alkali metals, alkaline earth metals, and ammonium but particularly hydrogen, sodium, potassium, calcium, magnesium, and ammonium. The sulfo group —SO$_3$X, is preferably located on the last carbon atom of the $R^2$ group. The $R^2$ group can be substituted or unsubstituted. Substituents on the $R^2$ group are selected from those substituents which do not adversely affect the anticalculus activity of the copolymer. Preferred sulfoalkyl acrylates include 2-sulfoethyl methacrylate, 3-sulfopropyl acrylate, 3-sulfopropyl methacrylate, and bis-(3-sulfopropyl) itaconate.

Any cationic-containing monomer may be used. The preferred cationic-containing monomers are:

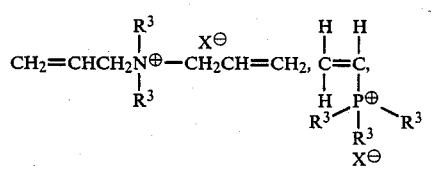

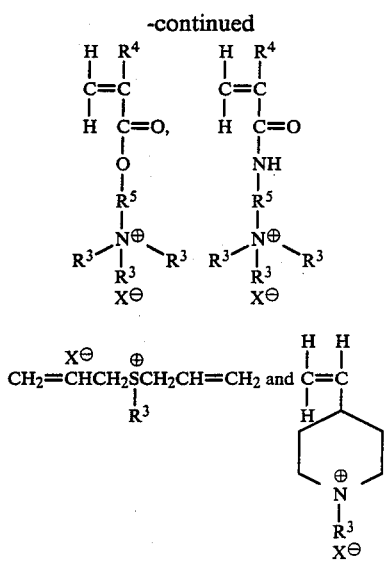

wherein $R^3$ is hydrogen, a phenyl, or an alkyl group of from 1 to 3 carbon atoms, $R^4$ is a hydrogen or an alkyl group of from 1 to 3 carbon atoms, preferably a hydrogen or methyl group, $R^5$ is a straight or branched chain of from 1 to 12 carbon atoms, preferably 1 to 3 carbon atoms; and X is an anion, preferably a halogen or alkyl sulfate. X may be any anion in the above formula. Examples include halogen, sulfate, sulfonate, phosphate, hydroxide, borate, cyanide, carbonate, thiocyanate, thiosulfate, isocyanate, sulfite, bisulfite, nitrate, nitrite, oxalate, silicate, sulfide, cyanate, acetate, and the other common inorganic and organic ions.

Specific examples of the most preferred cationic-containing monomers include diethyldiallyl ammonium chloride, dimethyldiallyl ammonium chloride, methacryloyloxy ethyl trimethyl ammonium methylsulfate and methacrylamido propyl trimethyl ammonium chloride. Mixtures of cationic-containing monomers may be used.

Copolymers of cationic monomers include 10 to 90% by weight of at least one carboxyl monomer selected from monounsaturated monocarboxylic and dicarboxylic acids of 3 to 5 carbon atoms, and salts thereof. Preferred comonomers in such copolymers are selected from acrylic acid, methacrylic acid, and mixtures thereof.

The monomers can be prepared, if desired, in a conventional manner but they are commercially available and, therefore, can be purchased. Polymerization of the monomers results in an essentially non-crosslinked random copolymer, the molecular weight of which can be adjusted with a little trial and error. The copolymer is preferably formed in a high yield ranging from about 50% to about 99% by weight of the comonomers.

It is also a requirement that the agent be soluble in water. Thus, high solubility of the agents is not essential but desirable. The antihydrolysis agent can be shipped in drums as a concentrated aqueous solution containing in the range of about 20% to about 50% by weight of solids per 100 parts of solution, which requires solubility to the extent of at least 20 weight parts per 100 parts of water.

Polymerization of the monomers identified herein can be carried out in a mutual solvent for both, such as in a lower alkanol of about 1 to 6 carbon atoms, or in water, with an effective amount of a free radical initiator sufficient to produce the desired composition within an acceptable period of time.

The reaction is conveniently carried out in water as the only reaction medium at a temperature in the range of about 30° to about 130° C. usually at atmospheric or slightly elevated pressure. The concentration of the copolymer formed may range from about 5% to about 50% by weight, based on total solids, which solution can be shipped directly.

The linear molecularly dehydrated polyphosphate salts operative herein are well known, being generally employed in the form of their wholly or partially neutralized water soluble alkali metal (e.g. potassium and preferably sodium) or ammonium salts, and any mixtures thereof. Representative examples include sodium hexametaphosphate, sodium tripolyphosphate, disodium diacid, trisodium monoacid, tetrasodium pyrophosphates, and the like. Linear polyphosphates correspond to $(NaPO_3)n$ where n is about 2 to about 125. When n is at least 3 in $(NaPO_3)n$, said polyphosphates are glassy in character.

An effective amount of at least one polyphosphate is used. This amount is generally 0.01 to 10% be weight of the entire composition, preferably 0.1 to 5%. The polyphosphates include alkali metal hexametaphosphates, alkali metal tripolyphosphates, dialkali metal diacids, trialkali metal monoacids, tetraalkali metal pyrophosphates, and mixtures thereof.

The polyphosphates can also function as polishing or abrasive agents. Although such polyphosphates are very effective against calculus in absence of enzyme found in saliva, in presence of enzyme, the polyphosphates are hydrolyzed to orthophosphates which are ineffective as anticalculus agents. By admixing the antihydrolysis homopolymers with one or more polyphosphates, hydrolysis of the polyphosphate to orthophosphate is thus inhibited and the action of the polyphosphate as anticalculus agent is preserved.

The sources of fluoride ions, or fluorine-providing compounds, required according to this invention as an essential component of the described composition, are well known in the art as anti-caries agents and also act as such agents in the practice of this invention. These compounds may be slightly soluble in water or may be fully water-soluble. They are characterized by their ability to release fluoride ions in water and by freedom from undesired reaction with other compounds of the oral preparation. Among these materials are inorganic fluoride salts, such as soluble alkali metal and alkaline earth metal salts, for example, sodium fluoride, potassium fluoride, ammonium fluoride, calcium fluoride, copper fluorides such as cuprous fluoride, zinc fluoride, barium fluoride, sodium fluorosilicate, ammonium fluorosilicate, sodium fluorozirconate, sodium monofluorophosphate, aluminum mono- and di-fluorophosphate, and fluorinated sodium calcium pyrophosphate. Alkali metal and tin fluorides, such as sodium and stannous fluoride, sodium monofluorophosphate, and mixtures thereof, are preferred.

The amount of fluorine-providing compound is dependent to some extent upon the type of compound, its solubility, and the type of oral composition, but it must be a nontoxic amount, generally about 0.005 to about 3.0% in the composition. In a dentifrice composition, e.g. gel, cream, toothpaste or toothpowder, an amount of such compound which releases 50 to 3500 ppm of flourine ion by weight of the composition is considered satisfactory. Any suitable minimum amount of such compound may be used but it is preferable to employ sufficient compound to release about 300 to about 2,000 ppm, more preferably about 800 to about 1,500 ppm of fluoride ion. Typically, in the case of alkali metal fluorides and stannous fluoride, this component is present in an amount up to about 2% by weight, based on the weight of the composition, and preferably in the range of about 0.05% to 1%. In the case of sodium monofluorophosphate, the compound may be present in an amount of about 0.1-3%, more typically about 0.2-1%.

In oral compositions such as mouthwashes, lozenges and chewing gum, the fluorine-providing compound is typically present in an amount sufficient to release up to about 500 ppm, preferably about 25 to about 300 ppm by weight of fluoride ion. Generally, about 0.005 to about 1.0% by weight of such compound is present.

Water employed in the preparation of commercially suitable oral compositions should preferably be of low ion content and free of organic impurities. Water comprises from about 2% to about 95%, preferably from about 20% to about 95% of the compositions of this invention. When in the form of toothpastes, the amount of water is preferably from about 2% to about 45%, while mouthwashes preferably contain from about 45% to about 95%.

In a toothpaste, the liquid vehicle may comprise water and humectant typically in an amount ranging from about 10% to about 90% by weight of the preparation. Glycerine, propylene glycol, sorbitol, polypropylene glycol and/or polyethylene glycol exemplify suitable humectants or carriers. Also advantageous are liquid mixtures of water, glycerine and sorbitol. In clear gels, where the refractive index is an important consideration, about 3–30% by weight of water, 0 to about 80% by weight of glycerine, and about 20–80% by weight of sorbitol, is preferably employed.

In certain desirable forms of this invention, the oral compositions may be substantially solid or pasty in character, such as toothpowder, a dental tablet, toothpaste, gel or dental cream. The vehicle of such solid or pasty oral preparations generally contains a polishing material. Examples of polishing materials are water-insoluble sodium metaphosphate, potassium metaphosphate, tricalcium phosphate, dehydrated calcium phosphate, anhydrous dicalcium phosphate, calcium pyrophosphate, magnesium orthophosphate, trimagnesium phosphate, calcium carbonate, aluminum silicate, zirconium silicate, silica, bentonite, and mixtures thereof. Other suitable polishing materials include the particulate thermosetting resins described in U.S. Pat. No. 3,070,510 such as formaldehydes of melamine, phenol, and urea, and cross-linked polyepoxides and polyesters. Preferred polishing materials include crystalline silica having particle size of up to about 5 microns, a mean particle size of up to about 1.1 microns, and a surface area of up to about 50,000 cm$^2$/gm. Also especially suitable are silica gel or colloidal silica, and complex amorphous alkali metal aluminosilicate.

When visually clear gels are employed, a polishing agent of colloidal silica and alkali metal aluminosilicate complexes are particularly useful since they have refractive indices close to the refractive indices of the liquid gelling agent.

The linear, molecularly dehydrated polyphosphate salts operative herein as abrasive dental additives are well known, being generally employed in the form of their wholly or partially neutralized water soluble alkali metal or ammonium salts and mixtures thereof. Representative examples include sodium hexametaphosphate, sodium tripolyphosphate, disodium diacid, trisodium monoacid, and tetrasodium pyrophosphates, and the like. Linear polyphosphates correspond to $(NaPO_3)n$ where n is about 2 to about 125. They are generally employed in the instant oral compositions in approximate weight amounts of 0.1 to 7%, preferably 1 to 5%.

The polishing material or dental abrasive is generally present in the solid or pasty compositions in weight concentrations of about 10% to about 99%. Preferably, it is present in amounts ranging from about 10% to about 75% in toothpaste, and from about 70% to about 99% in toothpowder.

Toothpastes, creams and gels typically contain a natural or synthetic thickener or gelling agent in proportions of about 0.1 to about 10, preferably about 0.5 to about 5, weight percent. A suitable thickener is synthetic hectorite, a synthetic colloidal magnesium, alkali metal silicate complex clay, and carboxyvinyl polymer or polyacrylic acid of intermediate molecular weight.

The oral compositions of this invention can contain a variety of optional conventional oral ingredients. Such optional ingredients include sudsing agents, flavoring agents, sweetening agents, binding agents, coloring agents, humectants, and pigments.

A preferred optional ingredient is a sudsing agent. Suitable sudsing agents are those which are reasonably stable and form suds throughout a wide pH range, i.e., non-soap anionic, cationic, zwitterionic and amphoteric organic synthetic detergents. Sudsing agents of these types are described more fully in Agricola et al U.S. Pat. No. 3,959,458 and in Haefele U.S. Pat. No. 3,937,807.

Flavoring agents can also be added to the instant compositions. Suitable flavoring agents include oil of wintergreen, oil of peppermint, oil of spearmint, oil of sassafras, and oil of clove. Sweetening agents which can be used include saccharin, dextrose, levulose, aspartame, D-tryptophan, dihydrochalcones, acesulfame and sodium cyclamate. Flavoring agents are generally used in the compositions at levels of from about 0.4% to about 2% by weight and sweetening agents at levels of from about 0.1% to about 5% by weight.

Binders can also be used with the toothpastes of the present inventions. Such binders include, for example, xanthan gum, carrageenan (Irish moss), and carboxyvinyl polymers or polyacrylic acids of intermediate molecular weight. These binders are generally present at a level of from about 0.1% to 1%.

Another optional component of the compositions herein is a humectant. The humectant serves to keep the toothpaste compositions from hardening upon exposure to air and in mouthwashes, give a moist feel to the mouth. Certain humectants can also impart desirable sweetness or flavor to mouthwash and toothpaste compositions. The humectant, on a pure humectant basis, generally comprises from about 0% to 70%, preferably from about 5% to 55%, by weight of the compositions herein.

Suitable humectants for use in this invention include edible polyhydric alcohols such as glycerine, sorbitol, xylitol and propylene glycol. Sorbitol is frequently employed as a 70% aqueous solution.

The mouthwashes herein may also contain ethanol in an amount of from about 0 to about 30%, preferably 5 to 25%, as a germicide.

The pH of the compositions herein is in the range of 6 to 10, preferably from 7 to 9. The pH is preferably achieved through a proper balancing of the pyrophosphate salts or by the addition of an alkaline or acidic agent.

The compositions herein are made using conventional mixing techniques.

In certain forms of the invention, the oral composition may be substantially liquid in character, such as mouthwash or rinse. In such a composition, the vehicle is typically a water-alcohol mixture which desirably includes a humectant. Generally, the weight ratio of water to alcohol is is the range of from about 1:1 to about 20:1, preferably about 3:1 to 10:1 and more preferably about 4:1 to about 6:1. The total amount of water-alcohol mixture in this type of preparation is typically in the range of from about 70% to about 99.9% by weight of the preparation.

The following examples further describe and demonstrate preferred embodiments within the scope of the present invention. The examples are given solely for the purpose of illustration and are not to be construed as limitations of this invention. Many variations thereof are possible without departing from the invention's spirit and scope.

EXAMPLE 1

This example demonstrates enzymatic hydrolysis inhibition by certain of the herein-disclosed antihydrolysis agents compared to Gantrez-S97 resin, which is a commercial antihydrolysis copolymer of methoxyethylene and maleic anhydride.

Enzymatic hydrolysis was conducted in a 25 ml buffered solution of tris(hydroxymethyl)amino-methane-HCl, $2.5 \times 10^{-3}$M at pH=7.20 containing 12.5 ppm of tetrasodium pyrophosphate. A known amount of the antihydrolysis agent was added to the pyrophosphate solution followed by the addition of inorganic pyrophosphatase enzyme. Solutions were continuously stirred at 25° C. After 3 hours, solutions were analyzed for orthophosphate using standard colorimeteric method. Inhibition of enzymatic hydrolysis by antihydrolysis agent was calculated according to the following equation:

$$\text{enzymatic hydrolysis inhibition} = \frac{(\text{phosphate})_c - (\text{phosphate})_a}{(\text{phosphate})_c},$$

where $(\text{phosphate})_c$ and $(\text{phosphate})_a$ represent orthophosphate concentrations in the absence and presence of antihydrolysis agent, respectively.

Results from triplicate experiments in the absence of the agent showed the that amount of orthophosphate released during enzymatic hydrolysis was greater than 95% of the available orthophosphate. Results showing effectiveness of the antihydrolysis agents in the presence of enzyme, are set forth in Table A, below:

TABLE A

| Anticalculus Agent | Composition | Mol. Wt. | Dosage (ppm) | Enzymatic Hydrolysis Inhibition (%) |
|---|---|---|---|---|
| None | — | — | 0 | 0 |
| poly (Am) | 100 | 6,000 | 15 | 0 |
| poly (i-PrAm) | 100 | 10,000 | 15 | 55 |
| poly (AMPS) | 100 | 10,000 | 15 | 83 |
| poly (DMDAAC) | 100 | 6,000 | 15 | 61 |
| Gantrez-S97 resin | — | — | 15 | 9 |

In Table A, the following contractions appear:

| | | |
|---|---|---|
| Gantrez-S97 | = | copolymer of methoxyethylene and maleic anhydride |
| DMDAAC | = | dimethyldiallyl ammonium chloride |
| AMPS | = | 2-acrylamido-2-methylpropane sulfonic acid |
| Am | = | acrylamide |
| i-PrAm | = | isopropyl acrylamide |

The data shown in Table A, above, demonstrates effectiveness of the antihydrolysis agents to suppress enzymatic hydrolysis of a pyrophosphate, especially when compared to the commercial resin Gantrez-S97. The data in the above table also demonstrates ineffectiveness of homopolymer of acrylamide relative to the homopolymer of isopropyl acrylamide, i.e., a substituted acrylamide. Whereas polyacrylamide yielded 0% enzymatic hydrolysis inhibition, poly (isopropyl acrylamide) yielded 55%.

What is claimed:

1. An oral composition comprising
   (a) 0.005 to 3.0% of a fluoride source, based on the weight of said composition;
   (b) an effective amount of a dental abrasive containing 0.1 to 10% by weight of said composition of a polyphosphate effective to inhibit hydroxyapatite formation, said polyphosphate is selected from the group consisting essentially of alkali metal hexametaphosphates, alkali metal tripolyphosphates, dialkali metal diacids, trialkali metal monoacids, tetraalkali metal pyrophosphates, and mixtures thereof; and
   (c) 0.01% to 10% by weight of said composition of at least one antihydrolysis agent selected from homopolymers of substituted acrylamides, homopolymers of unsaturated sulfonic acids and salts thereof, and homopolymers and copolymers of cationic monomers; said substituted acrylamides are defined as follows:

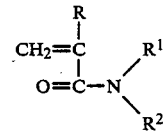

where R is hydrogen or methyl and $R^1$ and $R^2$ are individually selected from hydrogen, alkyl and substituted alkyl groups each containing a total of 1 to 12 carbon atoms, provided that $R^1$ and $R^2$ are not both hydrogens; wherein said cationic monomers are defined as follows:

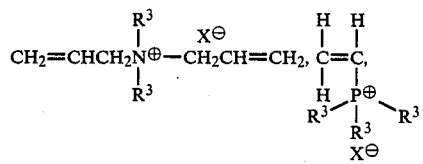

-continued

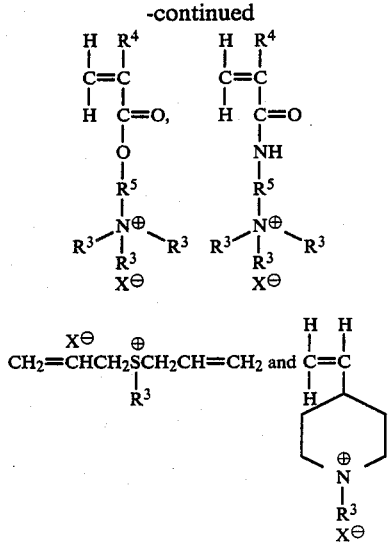

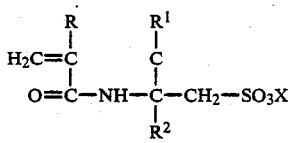

wherein $R^3$ is selected from hydrogen, phenyl group, and alkyl groups of from 1 to 3 carbon atoms, $R^4$ is selected from hydrogen and alkyl groups of from 1 to 3 carbon atoms; $R^5$ is selected from straight and branched chain groups of from 1 to 12 carbon atoms; and X is selected from anions.

2. Composition of claim 1 wherein said unsaturated sulfonic acids are selected from acrylamidoalkane sulfonic acids, styrene sulfonic acids, vinyl sulfonic acid, allyloxyhydroxyalkane sulfonic acids, sulfoloweralkyl acrylates, and salts and mixtures thereof.

3. Composition of claim 2 wherein in said substituted acrylamides, substituents on said alkyl groups are selected from allyl, aryl, hydroxyl, hydroxyalkyl, carboxylic acid, keto groups and mixtures thereof; wherein said unsaturated sulfonic acids are selected from acrylamidoalkane sulfonic acids and salts thereof defined as follows:

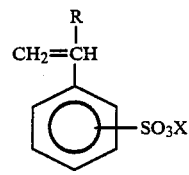

where R is selected from hydrogen and methyl; X is selected from hydrogen, ammonium, alkali metals, and alkaline earth metals; wherein in said cationic monomers, X is selected from hydrogen and alkyl sulfate groups, $R^4$ is selected from hydrogen and methyl, and $R^5$ is selected from straight and branched alkyl groups of 1 to 3 carbon atoms.

4. Composition of claim 3 wherein said substituted acrylamides are selected from tertiary butyl acrylamide, isopropyl acrylamide, isobutyl acrylamide, methyl acrylamide, tertiary butyl methacrylamide, 2-(2,4,4-trimethyl pentyl) acrylamide, 2-(2-methyl-4-oxopentyl) acrylamide, hydroxymethyl acrylamide, hydroxypropyl acrylamide, diacetone acrylamide, 3-acrylamido-3-methyl butanoic acid, and mixtures thereof; wherein in said unsaturated sulfonic acids, X is selected from hydrogen, ammonium, and alkali metals, R is hydrogen, and $R^1$ and $R^2$ are individually selected from alkyl groups of 1 to 3 carbon atoms; and wherein said cationic monomers are selected from diethyldiallyl ammonium chloride, dimethyldiallyl ammonium chloride, methacryloyloxy ethyl trimethyl ammonium methylsulfate, methacrylamido propyl trimethyl ammonium chloride, and mixtures thereof.

5. Composition of claim 4 wherein said copolymers of said cationic monomers contain at least one comonomer in polymerized form in amount of 10 to 90% by weight selected from acrylic acid, methacrylic acid, salts thereof, and mixtures thereof.

6. Composition of claim 4 wherein amount of said fluoride source is 0.005 to 3.0% by weight of said composition, wherein amount of said carboxylic monomer is 40 to 90% in said copolymers, and wherein molecular weight of said homopolymers and said copolymers is in the range of about 100 to 100,000.

7. Composition of claim 5 wherein amount of said fluoride source is 0.05 to 1%, and wherein amount of said antihydrolysis agent is 0.1 to 5%.

8. Composition of claim 2 wherein said styrene sulfonic acids and salts thereof are defined as follows:

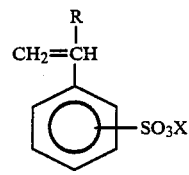

where R is selected from hydrogen and alkyl groups of 1 to 6 carbons, and X is selected from hydrogen, alkali metals, alkaline earth metals and ammonium radicals; wherein vinyl sulfonic acid and salts thereof are defined as follows:

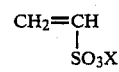

where X is selected from hydrogen, alkali metals, alkaline earth metals and ammonium radicals; wherein said allyloxyhydroxyalkane sulfonic acids and salts thereof are defined as follows:

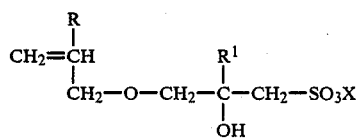

where R and $R^1$ are individually selected from hydrogen and methyl, and X is selected from hydrogen, alkali metal, alkaline earth metal, and ammonium groups; and wherein said sulfoalkyl acrylates are defined as follows:

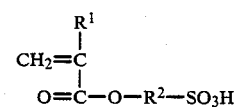

where $R^1$ is selected from hydrogen, methyl, and the group defined as

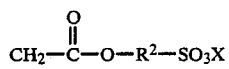

where R² is selected from alkylene groups of 1 to 12 carbon atoms and X is selected from hydrogen, alkali metals, alkaline earth metals, and ammonium radicals.

9. Composition of claim 5 having pH of 6 to 10 wherein amount of said fluoride source is sufficient to supply from about 50 ppm to about 2,500 ppm of fluoride ions; wherein amount of said antihydrolysis agent is 1 to 1000 ppm; wherein amount of said dental abrasive is 10 to 99%; and wherein said composition also includes an oral vehicle.

10. Composition of claim 9 wherein amount of said abrasive is 10 to 75% by weight, all or part of which is a polyphosphate selected from alkali metal hexametaphosphate, alkali metal tripolyphosphate, dialkali metal diacid, trialkali metal monoacid, tetraalkali metal pyrophosphate, and mixtures thereof.

11. Composition of claim 10 wherein said antihydrolysis agent is selected from the following:
 (a) homopolymer of isopropyl acrylamide having weight average molecular weight of about 10,000;
 (b) homopolymer of 2-acrylamido-2-methylpropane sulfonic acid having weight average molecular weight of about 10,000; and
 (c) homopolymer of dimethyldiallyl ammonium chloride having weight average molecular weight of about 6,000.

12. Composition of claim 1 wherein said antihydrolysis agent is selected from the following:
 (a) homopolymer of isopropyl acrylamide having weight average molecular weight of about 10,000;
 (b) homopolymer of 2-acrylamido-2-methylpropane sulfonic acid having weight average molecular weight of about 10,000; and
 (c) homopolymer of dimethyldiallyl ammonium chloride having weight average molecular weight of about 6,000.

13. Composition of claim 8 wherein said antihydrolysis agent has weight average molecular weight of 500 to 50,000.

14. Composition of claim 8 in toothpaste form containing 0.01 to 10% by weight of a polyphosphate selected from alkali metal hexametaphosphates, alkali metal tripolyphosphates, dialkali metal diacids, trialkali metal monoacids, tetraalkali metal pyrophosphates, and mixtures thereof; wherein said fluoride source is selected from sodium fluoride, stannous fluoride, sodium monofluorophosphate, and mixtures thereof; amount of said dental abrasive is 10 to 75% and said dental abrasive is selected from silica, hydrated aluminum, insoluble metaphosphates, thermosetting polymerized resins, and mixtures thereof; and amount of said oral vehicle is 10 to 90% by weight.

15. Method of inhibiting dental calculus comprising applying to oral cavity composition as defined in claim 1.

16. Method of inhibiting dental calculus comprising applying to oral cavity composition as defined in claim 3.

17. Method of inhibiting dental calculus comprising applying to teeth composition as defined by claim 4.

18. Method comprising applying to teeth composition as defined by claim 6.

19. Method comprising applying to teeth composition as defined by claim 14.

* * * * *